(12) United States Patent
Endermann et al.

(10) Patent No.: US 9,205,424 B2
(45) Date of Patent: Dec. 8, 2015

(54) DEVICES FOR DETERMINING THE PLATELET FUNCTION IN A CENTRIFUGAL ANALYZER

(75) Inventors: Joerg Endermann, Gladenbach (DE); Andreas Rechner, Marburg (DE); Norbert Zander, Marburg (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 0 days.

(21) Appl. No.: 13/421,468

(22) Filed: Mar. 15, 2012

(65) Prior Publication Data
US 2012/0237960 A1     Sep. 20, 2012

(30) Foreign Application Priority Data
Mar. 15, 2011    (EP) .................................. 11158195

(51) Int. Cl.
G01N 9/30      (2006.01)
B01D 45/00     (2006.01)
B04B 1/00      (2006.01)
B01L 3/00      (2006.01)
G01N 33/86     (2006.01)

(52) U.S. Cl.
CPC .............. *B01L 3/5021* (2013.01); *G01N 33/86* (2013.01); *B01L 2300/0681* (2013.01); *B01L 2400/0409* (2013.01)

(58) Field of Classification Search
CPC ............ G01N 33/86; G01N 2800/222; G01N 2800/52; A61J 1/1406; A61K 38/00; B01L 2200/142; B01L 2300/042; B01L 2300/049; B01L 2300/0681; B01L 2400/0409; B01L 2400/0638; B01L 3/5021; B01L 3/50825; B65D 51/002

USPC .......... 422/72, 533; 210/193, 500.21, 500.24, 210/512.1, 645, 777, 321.75; 435/343
See application file for complete search history.

(56) References Cited

U.S. PATENT DOCUMENTS

| | | | |
|---|---|---|---|
| 5,869,347 A | 2/1999 | Josef et al. | |
| 5,888,826 A * | 3/1999 | Ostgaard et al. | 436/69 |
| 7,087,177 B2 | 8/2006 | Min et al. | 210/782 |
| 7,708,152 B2 * | 5/2010 | Dorian et al. | 210/512.3 |
| 2007/0102374 A1 | 5/2007 | Kolenbrander et al. | 210/787 |
| 2009/0186341 A1 | 7/2009 | Dahm | |
| 2010/0226909 A1 * | 9/2010 | Hecker | C07K 1/34 424/94.63 |
| 2010/0330605 A1 * | 12/2010 | Rendu et al. | 435/29 |
| 2012/0156278 A1 * | 6/2012 | Beretta et al. | 424/443 |

FOREIGN PATENT DOCUMENTS

| | | | | |
|---|---|---|---|---|
| CN | 1736497 A | 2/2006 | | A61M 1/38 |
| CN | 1945310 A | 4/2007 | | G01N 30/02 |

(Continued)

OTHER PUBLICATIONS

European Search Report of European Patent Application No. EP 11 15 8195 issued on Sep. 7, 2011.
Uchiyama, S. et al., "Filter bleeding time: A new in vitro test of hemostasis I. Evaluation in normal and thrombocytopenic subjects", Thrombosis Research 1983, 31: p. 99-115.

(Continued)

*Primary Examiner* — Dean Kwak
(74) *Attorney, Agent, or Firm* — Slayden Grubert Beard PLLC

(57) ABSTRACT

The invention lies in the field of platelet function diagnostics and relates to devices and methods for determining the platelet function in a centrifugal analyzer.

12 Claims, 4 Drawing Sheets

(56) References Cited

FOREIGN PATENT DOCUMENTS

| | | | | |
|---|---|---|---|---|
| CN | 1964753 A | 5/2007 | ............. | A61M 1/36 |
| CN | 101248012 A | 8/2008 | ................ | C02F 1/38 |
| EP | 0797097 A1 | 9/1997 | | |
| EP | 1693109 A1 | 8/2006 | | |
| GB | 2175691 A | 12/1986 | | |
| WO | 9600899 A1 | 1/1996 | | |
| WO | 9734698 A1 | 9/1997 | | |

OTHER PUBLICATIONS

Krischek, B. et al., "Role of retention test Homburg in evaluating platelet hyperactivity and in monitoring therapy with antiplatelet drugs", Seminars in Thrombosis and Hemostasis 2005, 31(4): p. 458-463.

Krischek, B. et al., "Adhesion, spreading, and aggregation of platelets in flowing blood and the reliability of the retention test Homburg", Seminars in Thrombosis and Hemostasis 2005, 31(4): p. 449-457.

* cited by examiner

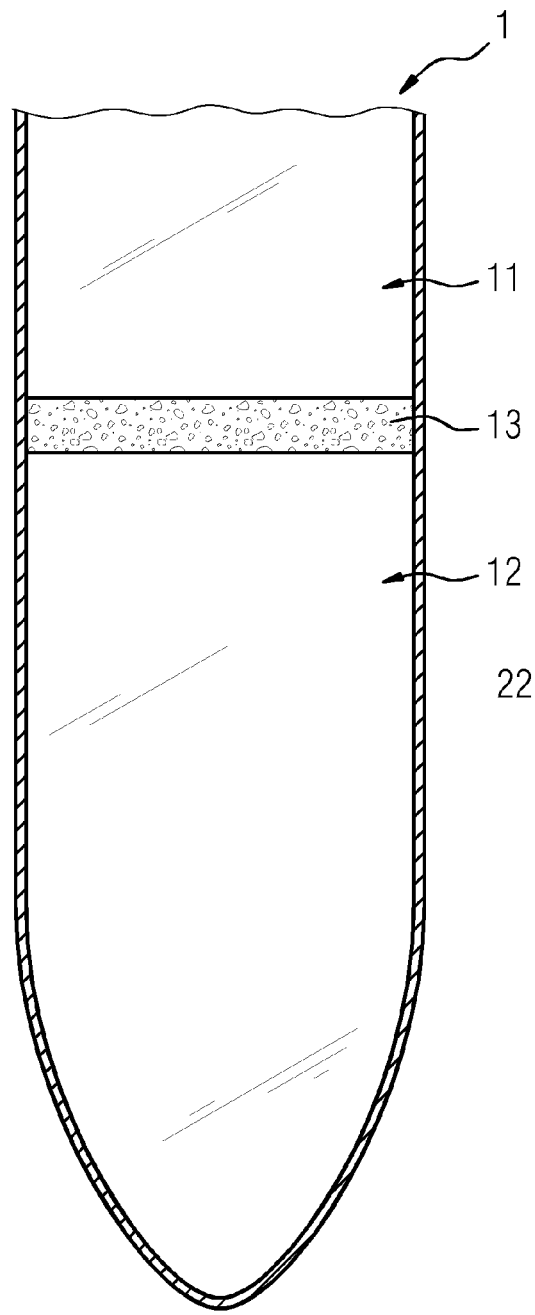
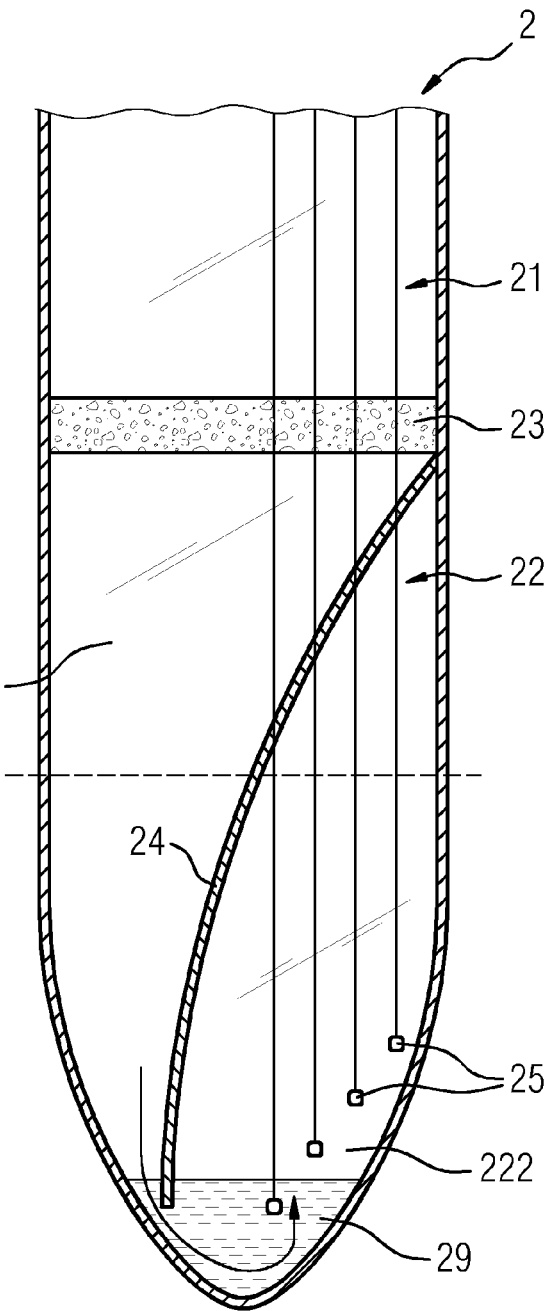

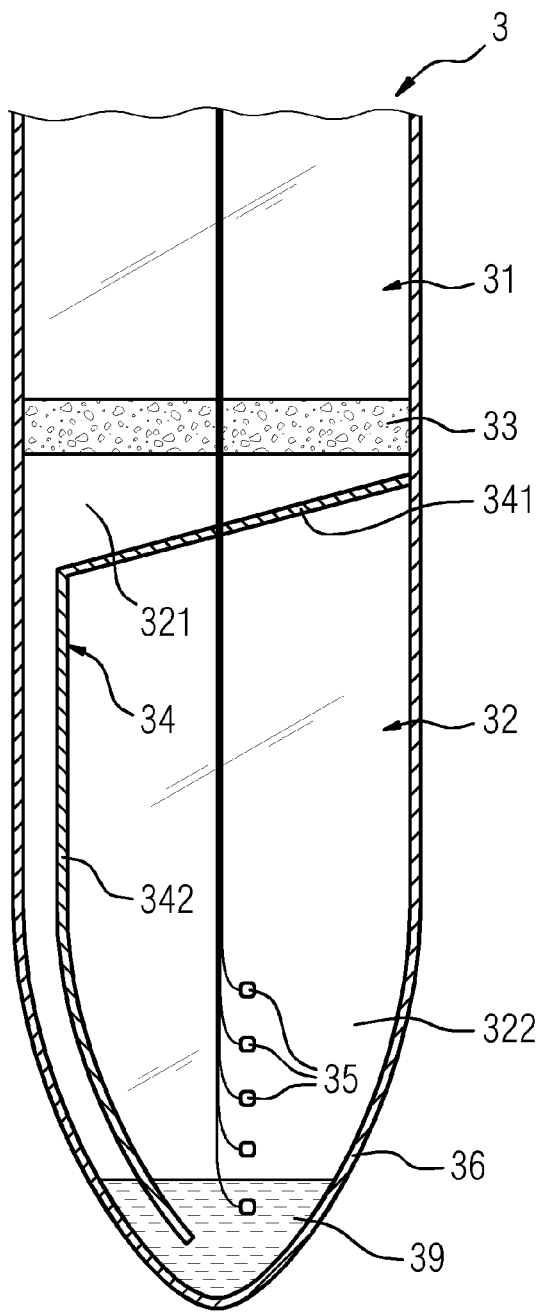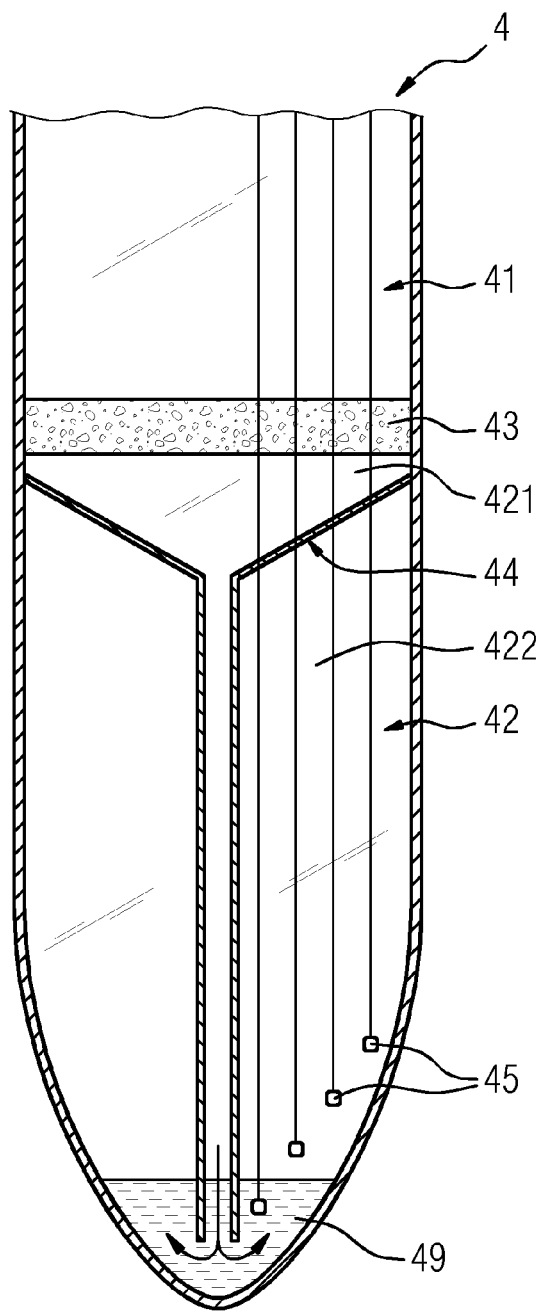

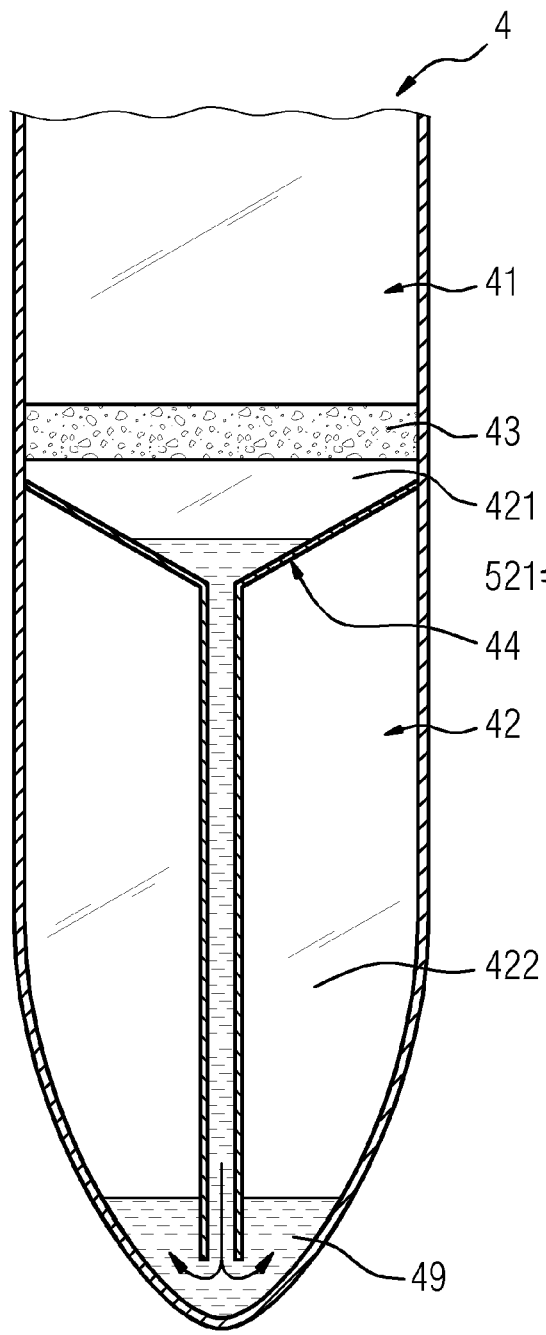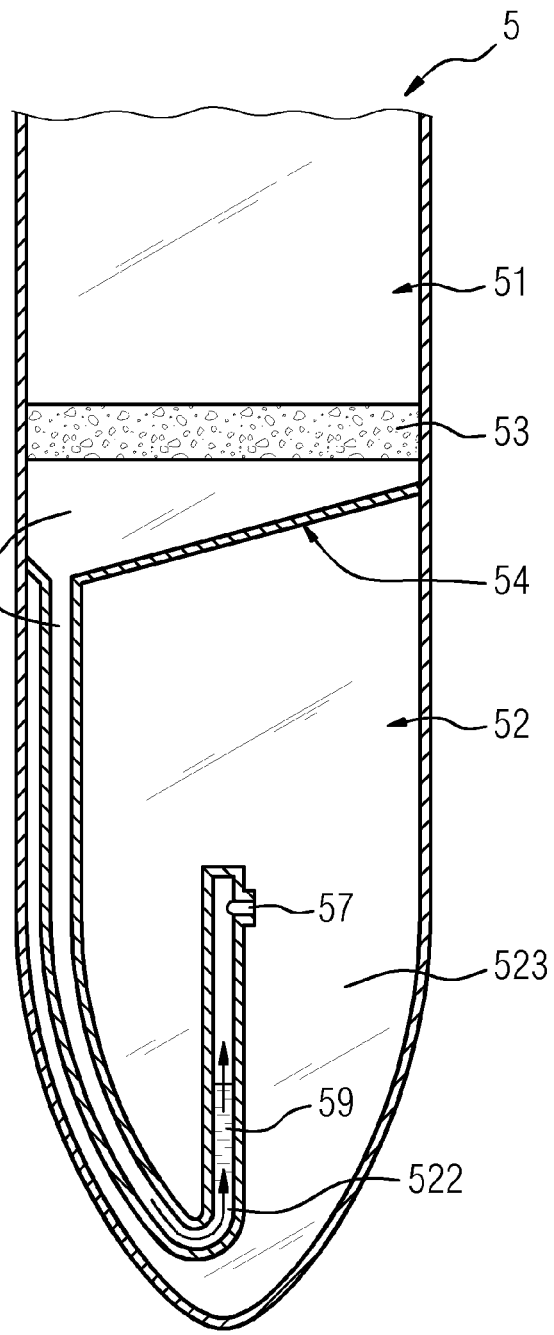

DEVICES FOR DETERMINING THE PLATELET FUNCTION IN A CENTRIFUGAL ANALYZER

PRIORITY STATEMENT

The present application hereby claims priority under 35 U.S.C. §119 of European Patent Application Number 11158195.5 filed Mar. 15, 2011, the entire contents of which are hereby incorporated herein by reference.

FIELD OF INVENTION

The present invention lies in the field of coagulation diagnostics, more precisely in the field of platelet function diagnostics, and relates to devices and methods for determining the platelet function in a centrifugal analyzer.

BACKGROUND OF INVENTION

Physiological processes, which firstly ensure the fluidity of the blood in the vessel system and secondly make sure that extravascular blood losses are avoided by forming blood clots, are encompassed by the term hemostasis. A plurality of protein factors and also cellular components such as e.g. platelets (thrombocytes) are involved in regulating hemostasis. In the case of vessel damage, platelets firstly accumulate on the subendothelial collagen. This adhesion is mediated by adhesion proteins, such as the von Willebrand factor (VWF). During the adhesion process, the platelets are activated and release mediators from their granules, as a result of which the aggregation of further platelets and an increase in the activation are induced. This brings about a primary vessel-wall occlusion (primary hemostasis), which is only stabilized by further reactions of the plasmatic coagulation system (secondary hemostasis). Dysregulation of these processes can lead to thrombophilia or a tendency toward hemorrhage, and, depending on the degree of severity, can have life-threatening consequences.

Various in vitro test methods were developed in coagulation diagnostics and these can be used to determine whether the blood of a patient can coagulate properly or whether there is a coagulation defect. In the case of a coagulation defect, it is often necessary to obtain more precise information in respect of the cause of the present defect in order to be able to select the optimum therapeutic measures. An important sub-function of the coagulation system, which can be examined in targeted fashion, is primary hemostasis, which substantially depends on the function of the platelets.

Determining the function of the thrombocytes or platelets is a conventional object in hemostasis diagnostics and it is important in a multiplicity of clinical situations, e.g. in the early detection of cardiovascular diseases, for diagnosing hereditary or acquired platelet function defects, for ruling out bleeding complications prior to surgical interventions or for monitoring antithrombotic therapies. Medication that inhibits the aggregation of platelets is primarily used for prophylaxis and therapy of arterial thromboembolic events, such as a myocardial infarction or stroke. The most widespread drugs with platelet aggregation inhibiting effects are acetylsalicylic acid (ASA, Aspirin®) and the thienopyridines clopidogrel and ticlopidine.

The prior art has disclosed various methods for examining the platelet function. Determining the bleeding time is a global in vivo test that detects primary hemostasis. The bleeding time is determined by inflicting a small cut or piercing injury on the patient and measuring the time until the bleeding stops. This is a roughly informative test that is difficult to to standardize and mainly used in emergency situations in order to obtain an overview of primary hemostasis. Intake of platelet aggregation inhibitors leads to an increase in the bleeding time. A disadvantage of determining the bleeding time is that it is not possible to rule out a platelet function defect in the case of a normal bleeding time.

Various in vitro methods allow a significantly more sensitive detection of platelet function defects. In these methods, the aggregation of the platelets is usually induced in a whole-blood sample or a sample of platelet-rich plasma (PRP) by adding an activator and/or by applying shear forces and the aggregation reaction is measured. The most commonly used activators, which are used for inducing the platelet aggregation, are the following: ADP (adenosine 5'-diphosphate), collagen, epinephrine (adrenalin), ristocetin and various combinations thereof, and also thrombin, thrombin receptor activating protein (TRAP) or serotonin. In order to apply shear forces in vitro, which shear forces are an important trigger for platelet aggregation in vivo, different methods are used, such as e.g. stirring the platelet sample or guiding or pressing the platelet sample through cannulae or apertures with a small diameter.

In the case of conventional light-transmission aggregometry (LTA), which is also referred to as Born platelet aggregation, the aggregation efficiency of the platelets in the platelet-rich plasma is measured photometrically in an aggregometer in the presence of aggregation-inducing substances. As a result of aggregate formation, the light-transmission of the PRP sample is increased and so measuring the light-transmission makes it possible to determine e.g. the rate of the aggregate formation. Light-transmission aggregometry also makes it possible to detect therapeutic effects of platelet aggregation inhibitors, which are used medicinally. A disadvantage of light-transmission aggregometry is that only platelet-rich plasma can be used as a sample material. Platelet-rich plasma not only lacks important constituents of the blood, such as e.g. red and white blood cells, but also requires a time-consuming and error-prone sample preparation.

The VerifyNow® system (Accumetrics) is a development of light-transmission aggregometry, which allows the examination of the platelet function in whole-blood samples. In this system, the aggregation reaction of the platelets is increased by the addition of fibrinogen-coated microparticles.

An entirely different test principle for determining the platelet function is realized in the platelet function analyzer (PFA-100®, PFA-200 Siemens Healthcare Diagnostics). This is a universal, automated and standardized in vitro whole-blood test in which primary hemostasis is measured under flow conditions and hence in the presence of strong shear forces. In order to simulate the flow conditions and the shear forces, as are prevalent in relatively small arterial blood vessels, negative pressure of approximately −40 mbar is generated in a special measuring cell and the citrated whole blood, which is situated in a sample reservoir, flows through a capillary with a diameter of approximately 200 μm. The capillary opens into a measurement chamber closed off by a partition member, e.g. a membrane, which contains a capillary-like central opening (aperture) through which the blood passes owing to the negative pressure. One or more activators, which induce platelet aggregation, are usually added to the membrane, at least in the region around the aperture such that the blood flowing past this comes into contact with the aggregation-inducing substances in the region of the aperture. As a result of the induced adhesion and aggregation of the platelets, a platelet plug (blood clot) is formed in the region of the aperture and it closes the membrane opening and stops the blood flow. In this system, the time required to seal the membrane opening is measured. This so-called closure time correlates with the functional efficiency of the platelets. A measuring cell for use in a method for determining the platelet function on the basis of the closure time is described in e.g. WO 97/34698. By way of example, use is made of measuring cells equipped with a membrane coated with collagen (Col) and, additionally, with either ADP or epinephrine (Epi). Various partition members and the production and use thereof are described in e.g. WO 96/00899 A1.

Another test principle, in turn, for determining the platelet function is based on the forced passage of blood or platelet-rich plasma through a filter.

Uchiyama, S. et al. (Thrombosis Research 31: 99-116, 1983) describe the so-called filter bleeding time (FBT) test. In this method, whole blood at constant pressure (approximately 150 mmHg) is guided through a polyester fiber filter (Dacron®). Platelet aggregates plug the filter pores and reduce the flow rate. The bleeding time FBT is the time that passes between the start of the flow and the time at which the flow rate has dropped to below one drop per 30 seconds.

GB 2175691 A describes a development of the FBT test according to Uchiyama et al. Here a whole-blood sample is made to pass through a filter consisting of a fiber mesh by means of positive pressure. The filter has pores with different dimensions and allows the passage of particles with a diameter of up to 10 µm. The effect of this is that the sample can be pressed through the filter at lower pressures of only 20 to 100 mmHg. Relatively large platelet aggregates plug the pores and increasingly block the passage of sample material. Determining the flow rate or comparing the number of platelets in the filtered eluate with the number of platelets in the unfiltered sample provide an insight into the aggregation efficiency of the platelets and hence into the platelet function.

Another method for determining the platelet function, which is based on the principle of the forced passage of blood or platelet-rich plasma through a filter, is the so-called retention test Homburg (RTH) (Krischek, B. et al., Seminars in Thrombosis and Hemostasis 31(4): 449-457, 2005; Krischek, B. et al., Seminars in Thrombosis and Hemostasis 31(4): 458-463, 2005). In this method, whole blood or platelet-rich plasma is passed through a Porex® filter unit by means of a centrifugal force (10 minutes at 110×g), which filter unit has a height of 2.3 mm and a pore dimension of 16-22 µm. The difference between the number of platelets before and after the sample has passed through the filter is determined and the retention index (RI %) is calculated. A reduced retention of platelets in the filter indicates a loss of platelet function. An increased retention of platelets in the filter indicates an enhanced platelet activity.

A disadvantage of the two last-mentioned methods is that the number of platelets must be determined twice in each sample, in addition to actually carrying out the test. For this purpose, firstly, special analysis equipment is required and, secondly, every sample must be processed a number of times.

Various commercially available instruments for automated coagulation diagnostics (coagulation analyzers) comprise a centrifugal unit. The latter usually consists of a cuvette rotor, on which a spectrophotometer unit is arranged such that the samples can be measured photometrically during the rotation of the cuvette rotor. It is therefore particularly desirable to provide a method for platelet diagnostics which could be carried out on the available instruments that have a centrifuge unit.

SUMMARY OF INVENTION

The present invention was therefore based on the object of providing a device and a method for determining the platelet function, which allow a reliable, simple and quick determination of the platelet function using a centrifugal analyzer.

This object is achieved by the technical features of the independent claims. The dependent claims specify further embodiments of the invention.

The present invention relates to a measuring cell for determining the platelet function, the measuring cell comprising the following components:

a first chamber for accommodating a platelet-containing liquid sample, a second chamber, which catches the liquid sample from the first chamber provided that a centrifugal force acts on the measuring cell, and a porous partition member, which separates the first and second chambers from one another, and wherein the partition member contains at least one soluble substance that influences the platelet activity.

BRIEF DESCRIPTION OF THE DRAWINGS

A more complete appreciation of the present invention and many of the attendant advantages thereof will be readily understood by reference to the following detailed description when taken in conjunction with the accompanying drawings, in which:

FIG. 1 shows an embodiment of a measuring cell according to the invention.

FIG. 2 shows another embodiment of a measuring cell according to the invention.

FIG. 3 shows a further embodiment of a measuring cell according to the invention.

FIG. 4 shows a further embodiment of a measuring cell according to the invention.

FIG. 5 shows a further embodiment of a measuring cell according to the invention.

DETAILED DESCRIPTION OF INVENTION

Figure 6:
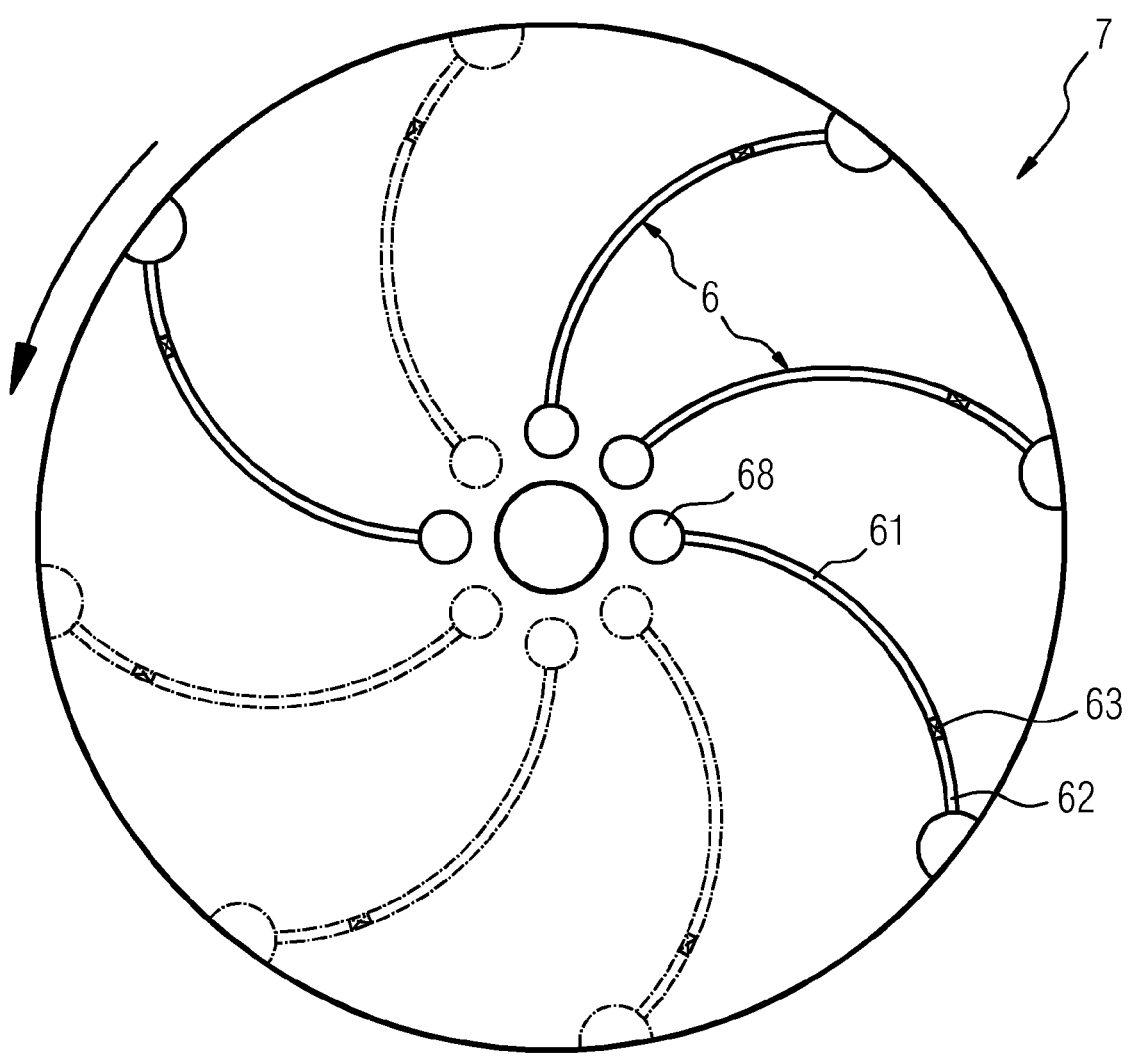
FIG. 6 shows a plan view of a measuring-cell rotor according to the invention.

The terms "thrombocytes" and "platelets" are used synonymously.

The term "platelet-containing liquid sample" should be understood to mean a liquid sample that contains human or animal platelets, more particularly whole blood, platelet-rich plasma (PRP) or other platelet preparations. The whole-blood sample is preferably freshly taken, venous, anticoagulated human or animal blood. The whole blood is preferably anti-coagulated by addition of an anticoagulant. The following are suitable for use as anticoagulants: buffered, calcium-binding citrate solutions, such as e.g. 3.2 or 3.8% buffered sodium citrate solutions, EDTA, heparin and natural or synthetic direct thrombin inhibitors such as e.g. hirudin, PPACK (D-Phe-Pro-Arg-chloromethyl ketone, HCl) argatroban and melagatran, or natural or synthetic direct Factor Xa inhibitors, such as e.g. antistasin, tick anticoagulant peptide, yagin, draculin, GGACK (H-Glu-Glu-Arg-chloromethyl ketone), diamidino Factor Xa inhibitors and monobenzamidine Factor Xa inhibitors.

The term "porous partition member" should be understood to mean a divider which completely separates the first and second chambers from one another and which consists of a material that allows the passage of individual blood cells but prevents the passage of cell aggregates, in particular platelet aggregates of aggregated platelets. To this end, the material preferably has a pore dimension of 2-20 µm, particularly preferably of 5 µm. Moreover, the partition member is undamaged, i.e. it has no perforations, cuts or apertures of any type.

The porous partition member contains at least one substance that influences the platelet activity, which substance is soluble in the liquid sample when a platelet-containing liquid sample is brought into contact with the partition member.

The partition member is preferably embodied in the form of a membrane. The preferred material is liquid absorbent, and so the substances that influence the platelet activity can be applied in solution. Particularly preferred materials are cellulose esters, ceramics, nylon, polypropylene, polyether sulfone, and polyvinylidene fluoride (PVDF). The porous partition member wetted or soaked with the desired substances is preferably dried. As a result of the liquid sample contacting the partition member, the substances are dissolved from the partition member and mix with the platelet-containing sample.

The term "the substance that influences the platelet activity" comprises substances that are able to induce or inhibit the aggregation of platelets.

In one embodiment, the porous partition member contains at least one platelet activator, preferably from the following group: ADP (adenosine 5'-diphosphate) 2-MeSADP (2-methylthioadenosine 5'-diphosphate), collagen, epinephrine, ristocetin, thrombin, TRAP (thrombin receptor activating protein), arachidonic acid, U46619 ((Z)-7-[(1S,4R,5R,6S)-5-[(E,3S)-3-hydroxyoct-1-enyl]-3-oxabicyclo[2.2.1]heptan-6-yl]hept-5-enoic acid), PMA (phorbol 12-myristate 13-acetate) and serotonin.

In another embodiment, the porous partition member contains at least one platelet inhibitor, preferably from the following group: prostaglandin E1 (PGE 1), prostaglandin 12, forskolin, iloprost and cicaprost.

In another embodiment, one or more substances from the group of platelet activators and the group of platelet inhibitors can be contained in the partition member. By way of example, the combination of ADP and PGE 1 is particularly suitable for determining the platelet activity in samples coming from patients who are being treated with an antithrombotic therapeutic agent from the group of P2Y(12) antagonists, such as e.g. clopidogrel or ticlopidine. A person skilled in the art is aware of which substances or substance combinations can be used to determine the platelet activity.

The measuring cell according to the invention preferably is an integral, preferably cylindrical or conical, hollow body, into which a porous partition member can be inserted in tailor-made fashion such that the partition member completely separates the first and second chambers from one another, i.e. over the whole diameter of the hollow body. The integral hollow body is preferably a tube with an internal diameter of between approximately 100 µm and 1 cm. The first chamber serves to accommodate a platelet-containing liquid sample and, to this end, has an opening. The second chamber serves to capture the liquid sample from the first chamber, which sample passes through the partition member, provided that a centrifugal force acts on the measuring cell.

Alternatively, the measuring cell according to the invention can be a two-part reaction vessel, which consists of a first hollow body, which is open on one side and forms the second chamber, and a second hollow body, which is open on two sides and forms the first chamber. The two hollow-body components are interconnected such that an opening of the second component is arranged on the one opening of the first component. The porous partition member is either applied precisely between these two components or in the one opening of the first component or in the opening of the second component facing the first component.

The integral reaction vessel or the components of the multipart reaction vessel preferably consist of a light-transmitting material, preferably of plastic or of glass.

In the interior of the second chamber, which, as seen from the porous partition member, has a proximal half and a distal half along the longitudinal axis thereof, a preferred embodiment of the measuring cell according to the invention has means for subdividing the space in the second chamber into a first portion and a second portion. The first portion serves to capture and transport the sample liquid that passes through the partition member. The sample liquid is transported into the distal from the proximal half of the second chamber. The second portion serves to measure the amount of liquid in the sample liquid caught in the second chamber. The first and the second portion are interconnected in the distal half of the second chamber such that the caught and transported sample liquid can pass into the second portion from the first portion. Subdividing the space in the second chamber into a first portion (capture region) and a second portion (measuring region) is advantageous in that the sample liquid, which passes through the partition member during the centrifugation, does not wet the whole second chamber in an uncontrolled fashion, which could lead to a fault in the measurement of the filling level or another parameter in the second measurement chamber. Subdividing the space in the second chamber into a first portion (capture region) and a second portion (measuring region) ensures that the sample liquid is caught, collected and transported to the distal region of the second chamber in a targeted fashion, which ensures that the sample liquid collects in the second portion (measuring region) from bottom (distal) to top (proximal) in the measuring-cell tip.

The means for subdividing the space in the second chamber into a first and a second portion can have various designs.

In a simple embodiment, the means for subdividing the space in the second chamber into a first and a second portion can have a plane that is at an angle relative to the porous partition member or merely consists of a continuous ramp with an angled plane, which extends from the proximal into the distal half of the second chamber.

In another embodiment, the means for subdividing the space in the second chamber into a first and a second portion has a first section, which has a plane that is at an angle relative to the porous partition member, and a second partial section, which follows the first partial section, runs substantially parallel to a wall delimiting the space in the second chamber and forms a tubular structure with said wall, which tubular structure extends into the distal half of the second chamber. This embodiment is advantageous in that the first portion of the second chamber (capture region) is reduced to a minimum of the space in the second chamber such that a space in the second chamber that is as large as possible is available for the second portion (measuring region). By way of example, this is advantageous in that the greatest possible amount of available area is available for possible measuring devices, which are arranged on the measuring cell.

In another embodiment, the means for subdividing the space in the second chamber into a first and a second portion has a funnel-like shape, and the tubular region of the funnel-like means extends into the distal half of the second chamber.

An embodiment of a measuring cell with means for subdividing the space in the second chamber into a first and a second portion can be designed such that the second portion of the second chamber (measuring region) has means for electrically measuring the filling level, preferably a plurality of electrode pairs.

Another embodiment of a measuring cell according to the invention has means for subdividing the space in the second chamber into a first, a second and a third portion. The first portion (capture region) serves to capture and transport the sample liquid, which passes through the partition member, along the longitudinal axis of the second chamber and into the distal from the proximal half. The first portion is connected to the second portion in the distal half of the second chamber such that the sample liquid caught and transported can pass into the second portion from the first portion. The second portion (measuring region) serves to measure the flow speed of the sample liquid captured in the second chamber. The second portion (measuring region) has the form of a capillary, which rises from the distal half in the direction of the proximal half of the second chamber and has an opening at its end, which opening establishes a connection to the third portion. The third portion (overflow region) serves as an overflow for the sample liquid from the second portion. This embodiment of a measuring cell is particularly suitable for determining the platelet function on the basis of measuring the flow speed of the sample liquid.

A further object of the present invention relates to a device for a centrifugal analyzer, which has at least two measuring cells according to the invention. Depending on the embodiment, such a device can have up to 100 measuring cells. The advantage of such a device consists of being able to carry out a number of platelet-function determinations at the same time. In the process, it is possible to determine simultaneously either a plurality of aliquots of one sample or aliquots of different samples. The plurality of measuring cells can either be similar or differ in terms of their structural designs or in terms of the coating of the partition members with substances that influence platelet activity.

One embodiment of a device for a centrifugal analyzer, which has at least two measuring cells according to the invention, is a disk, on which the measuring cells are arranged in an arc-like and radial fashion. In the following text, such a device is also referred to as a measuring-cell rotor.

In a special embodiment of a measuring-cell rotor, the measuring cells do not have a straight but rather a curved shape along their longitudinal axes. The advantage of this is that constant flow conditions prevail in the measuring cells during the rotation of the measuring-cell rotor. At least the region of a measuring cell containing the partition member preferably has a smaller diameter than the remaining regions of the measuring cell. This region preferably has a diameter of between approximately 50 and 500 µm.

A measuring-cell rotor according to the invention can for example consist of a light-transmitting plastic and/or be assembled from an upper part and a lower part. The sides of the upper and lower part facing one another in the assembled measuring-cell rotor can have recesses and/or elevations, which then form the desired measuring-cell shapes. The upper part contains a pipetting hole for each measuring cell and the sample material can be introduced into the first chamber of a measuring cell therethrough. Before the upper and lower parts are assembled, the porous partition member can either be inserted separately into every measuring cell as an individual unit or it can be inserted in the form of a continuous strip, made of a suitable porous material, which is arranged concentrically between the upper and lower parts and thus passes through all measuring cells of the rotor. Coating the porous material with one or more substances that influence the platelet activity can either take place before the separate partition members or the continuous strip are/is inserted, or it can take place in situ, i.e. when the partition members or the strip were/was already connected to the upper or lower part.

A measuring-cell rotor, which at least in part consists of a light-transmitting material, makes it possible to measure the amount of liquid caught in the second chamber or measure the flow speed of the sample liquid through the partition member by means of photometric methods. To this end, one or more light sources, preferably light-emitting diodes (LEDs), are preferably arranged above the measuring-cell rotor and respectively associated light detectors are preferably arranged below the measuring-cell rotor, or vice versa, such that the light can be beamed through the measuring regions of the measuring cells perpendicularly to the rotational plane.

A further object of the present invention is a method for determining the platelet function, in which use is made of a measuring cell according to the invention or a device that comprises at least two measuring cells according to the invention. The method comprises at least the following steps:

filling a platelet-containing liquid sample into the first chamber of a measuring cell according to the invention, applying a centrifugal force on the measuring cell with the liquid sample, measuring the amount of liquid caught in the second chamber or measuring the flow speed of the sample liquid through the partition member.

The amount of liquid (or the liquid volume) that passes through the partition member from the first chamber as a result of the centrifugal force acting thereon and is caught in the second chamber is inversely correlated to the platelet function.

The flow speed of the sample liquid, which passes through the partition member and is caught in the second chamber, is also inversely correlated to the platelet function.

As the platelet aggregation decreases as a result of a reduced platelet function and reduces the plugging of the pores in the partition member, the amount of sample liquid that can pass through the partition member in a given time interval increases and hence the flow speed or flow rate increases, and with it the amount of liquid caught in the second chamber.

As the platelet aggregation increases as a result of an enhanced platelet function and increases the plugging of the pores in the partition member, the amount of sample liquid that can pass through the partition member in a given time interval decreases and hence the flow speed or flow rate decreases, and with it the amount of liquid caught in the second chamber.

The centrifugal force, which, according to the invention, is applied to the measuring cell, preferably lies in a range of 50-2000×g. The centrifugal force can be applied with the aid of a conventional centrifugal unit.

The amount of liquid that passes through the partition member and is caught in the second chamber can be measured in different ways.

In a first embodiment, the amount of liquid caught in the second chamber is determined photometrically. To this end, at least one partial section of the second chamber in the measuring cell according to the invention consists of a light-transmitting material. Furthermore, a plurality of light sources, preferably light-emitting diodes (LEDs), and respectively associated light detectors are arranged along the longitudinal axis of the second chamber and perpendicular to the rotational plane of the measuring cell according to the invention or of the measuring-cell rotor according to the invention. During the measurement, the light sources emit light, the intensity I of which is measured by the detector respectively assigned to a light source. The light intensity is reduced if sample liquid is situated between the light source and detector. The absorbance $E=-\log(I_t/I_0)$ ($I_t$=light intensity at time t, $I_0$=light intensity at time $0$) is proportional to the amount of absorbing material between light source and detector. The relative positioning of the light sources with respect to the longitudinal axis of the second chamber provides a statement in respect of the sample volume flown through the partition member. The number of light source/detector pairs prescribes the discrimination of different volumes. In the simplest case (n=3), it is only possible to make a digital statement in respect of normal or pathological, when n=6 there are 5 possible volume discriminations. It is determined whether the absorbance at a given point is greater than a prescribed threshold (sample liquid in the beam path) or less than this threshold (air in the beam path). There is a simple relationship between the distance of a detector from the base of the vessel and the amount of liquid in the vessel. If a detector is at a distance h from the base of a cylindrical vessel with a radius r, large absorbance means a minimum amount of liquid in the vessel is given by $r^2\pi h$. Measuring the absorbance over time makes it possible to determine the amount of liquid in a time-dependent fashion: $V=V(t)$. Determining the time-dependent flow speed results from mathematically differentiating the overall amount of liquid with respect to time $(d/dt\ V(t))$.

In a second embodiment, the amount of liquid caught in the second chamber is determined electrically. To this end, a plurality of electrode pairs having different lengths for detecting the filling level are arranged on the second test chamber. As the liquid volume in the second chamber increases, more and more electrodes are in contact with the sample liquid. There is a simple relationship between the distance of an electrode from the base of the vessel and the amount of liquid in the vessel. The number of electrodes prescribes the discrimination of different volumes. In the simplest case (n=3), it is only possible to make a digital statement in respect of normal or pathological, when n=6 there are 5 possible volume discriminations. In the simplest case, a measurement is conducted via the conductivity (Ohmic measurement). No current flows if there is air between electrodes, between which there is a work potential, since air is an electric insulator. However, as the chamber fills with sample liquid, the respective circuit between the electrodes is able to be closed thereby because blood or plasma is electrically conductive as a result of dissolved salts.

In a third embodiment, the flow speed is determined by means of laser-Doppler anemometry (LDA). To this end, at least one partial section of the second chamber of the measuring cell according to the invention consists of a light-transmitting material. A laser beam is split into two beams, which are aligned such that they cross in a region of the second chamber. An interference pattern is created at the measuring point where the beams cross. A detector measures the two scattered waves, which are produced by the flowing sample liquid. The measurement signal is a superposition of the two scattered waves, as a result of which there are beats that are caused by the Doppler Effect, the frequency (Doppler frequency) of which beats is proportional to the speed of the flowing sample liquid.

The amount of liquid caught in the second chamber can be measured continuously over a given time interval. To this end, the time-dependent flow through the partition member is measured.

Alternatively, the amount of liquid caught in the second chamber can be measured once at a given time. By way of example, the measurement can be carried out by determining an end point. To this end, the total amount of liquid that has passed the partition member at a certain time is determined.

The platelet function in an unknown sample is preferably determined by comparing the measurement result from the sample with the measurement result of one or more controls with a known platelet activity. The controls/calibrators preferably consist of a collective of blood/plasma donations from healthy persons. The median is preferably determined from the measurement results that were determined for the samples from this collective, and the measurement result from an unknown sample is put into relation thereto.

Since the amount of sample liquid that passes through the partition member is inversely proportional to the platelet function, the inverse (1/V) of the amount of liquid V caught in the second chamber is particularly suitable as a measure for the platelet function. If the inverse 1/V of an unknown sample lies below a previously established median threshold, it is a sample with a reduced platelet function and a risk of hemorrhaging. If the inverse 1/V of an unknown sample lies above a previously established median threshold, it is a sample with an enhanced platelet function and a risk of thrombosis.

DESCRIPTION OF THE FIGURES

The present invention is explained in more detail by means of the illustrated figures, which are discussed below. It should be noted here that the figures are only of a descriptive nature and are not intended to restrict the invention in any way.

FIG. 1 shows an embodiment of a measuring cell (1) according to the invention. The measuring cell (1) comprises a first chamber (11) for accommodating a platelet-containing liquid sample and a second chamber (12), which catches the liquid sample from the first chamber provided that a centrifugal force acts on the measuring cell. The measuring cell furthermore comprises a porous partition member (13), which separates the first and second chambers from one another over the entire diameter of the hollow body. The partition member (13) contains at least one soluble substance that influences the platelet activity.

FIG. 2 shows another embodiment of a measuring cell (2) according to the invention. The measuring cell (2) comprises a first chamber (21) for accommodating a platelet-containing liquid sample and a second chamber (22), which catches the liquid sample from the first chamber provided that a centrifugal force acts on the measuring cell. The measuring cell furthermore comprises a porous partition member (23), which separates the first and second chambers from one another over the entire diameter of the hollow body. The partition member (23) contains at least one soluble substance that influences the platelet activity.

Moreover, in the second chamber (22), the measuring cell (2) shown here comprises means (24) in the form of a ramp-like element for subdividing the space in the second chamber into a first portion (221) and a second portion (222).

The first portion (221) serves to capture and transport the sample liquid that passes through the partition member. The second portion (222) serves to measure the amount of liquid in the sample liquid (29) caught in the second chamber (22). The first and second portions are interconnected in the distal half of the second chamber (i.e. below the dashed line) such that the caught and transported sample liquid can only in the vicinity of the measuring-cell tip pass into the second portion from the first portion. The advantage of this is that the sample liquid that passes the partition member (23) during the centrifugation does not wet the entire second chamber (24) in an uncontrolled fashion but rather the sample liquid is caught, collected and transported to the distal region of the second chamber in a targeted fashion. The sample liquid (29) transported thus collects in the second chamber (22), more particularly in the second portion (222) of the second chamber (22), from bottom (distal) to top (proximal) in the measuring-cell tip.

Moreover, the measuring cell (2) shown here comprises electrodes (25) of different lengths for detecting the filling level. As the liquid level increases in the second chamber (22), more particularly in the second portion (222) of the second chamber (22), more and more electrodes come into contact with the sample liquid.

FIG. 3 shows a further embodiment of a measuring cell (3) according to the invention. The measuring cell (3) comprises a first chamber (31) for accommodating a platelet-containing liquid sample and a second chamber (32), which catches the liquid sample from the first chamber provided that a centrifugal force acts on the measuring cell. The measuring cell furthermore comprises a porous partition member (33), which separates the first and second chambers from one another over the entire diameter of the hollow body. The partition member (33) contains at least one soluble substance that influences the platelet activity.

Moreover, in the second chamber (32), the measuring cell (3) shown here comprises means (34) for subdividing the space in the second chamber into a first portion (321) and a second portion (322).

The means (34) for subdividing the space in the second chamber (32) into a first and a second portion has a first section (341), which has a plane that is at an angle relative to the porous partition member. The means (34) furthermore has a second partial section (342), which follows the first partial section (341), runs substantially parallel to a wall (36) delimiting the space in the second chamber (32) and forms a tubular structure with said wall, which tubular structure extends into the distal half of the second chamber (32). This embodiment is advantageous in that the first portion (321) of the second chamber, the capture region, is reduced to a minimum of the space in the second chamber (32) such that a space in the second chamber (32) that is as large as possible is available for the second portion (322), the measuring region. By way of example, this is advantageous in that the greatest possible amount of available area is available for possible measuring devices, which are arranged on the measuring cell.

Furthermore, the measuring cell (3) shown here comprises electrodes (35) of different lengths for detecting the filling level. As the liquid level increases in the second chamber (32), more particularly in the second portion (322) of the second chamber (32), more and more electrodes come into contact with the sample liquid (39).

FIG. 4 shows a further embodiment of a measuring cell (4) according to the invention. The measuring cell (4) comprises a first chamber (41) for accommodating a platelet-containing liquid sample and a second chamber (42), which catches the liquid sample from the first chamber provided that a centrifugal force acts on the measuring cell. The measuring cell furthermore comprises a porous partition member (43), which separates the first and second chambers from one another over the entire diameter of the hollow body. The partition member (43) contains at least one soluble substance that influences the platelet activity.

Moreover, in the second chamber (42), the measuring cell (4) shown here comprises means (44) for subdividing the space in the second chamber into a first portion (421) and a second portion (422).

The means (44) for subdividing the space in the second chamber (42) into a first and a second portion has a funnel-like shape in this case, and the tubular region of the funnel-like means extends into the distal half of the second chamber (42).

The measuring cell (4) shown in FIG. 4A comprises electrodes (45) of different lengths for detecting the filling level.

In the measuring cell (4) shown in FIG. 4B, the walls of the measuring cell and at least the tubular region of the funnel-shaped means (42) consist of a light-transmitting material. This embodiment of a measuring cell is particularly suitable for measuring the flow speed of the sample liquid (49) in the second chamber of the measuring cell. The flow speed is then, in the tubular region of the funnel-shaped means (44), measured photometrically with the aid of light sources and light detectors (not illustrated) arranged along the longitudinal axis of the measuring cell. Alternatively, the flow speed in the tubular region of the funnel-shaped means (44) can also be measured by means of laser-Doppler anemometry (LDA).

FIG. 5 shows a further embodiment of a measuring cell (5) according to the invention. The measuring cell (5) comprises a first chamber (51) for accommodating a platelet-containing liquid sample and a second chamber (52), which catches the liquid sample from the first chamber provided that a centrifugal force acts on the measuring cell. The measuring cell furthermore comprises a porous partition member (53), which separates the first and second chambers from one another over the entire diameter of the hollow body. The partition member (53) contains at least one soluble substance that influences the platelet activity.

Moreover, in the second chamber (52), the measuring cell (5) shown here has means (54) for subdividing the space in the second chamber into a first portion (521), a second portion (522) and a third portion (523). The first portion (521), the capture region, serves to capture and transport the sample liquid, which passes through the partition member, along the longitudinal axis of the second chamber (52) and into the distal from the proximal half. The first portion (521) is connected to the second portion (522) in the distal half of the second chamber (52) such that the sample liquid caught and transported can pass into the second portion (522) from the first portion (521). The second portion (522), the measuring region, serves to measure the flow speed of the sample liquid captured in the second chamber (52). Here, the second portion (522) has the form of a capillary, which rises from the distal half in the direction of the proximal half of the second chamber and has an opening (57) at its end, which opening establishes a connection to the third portion (523). The third portion (523), the overflow region, serves as an overflow for the sample liquid (59) from the second portion (522). This embodiment of a measuring cell is particularly suitable for determining the platelet function on the basis of measuring the flow speed of the sample liquid.

FIG. 6 shows a plan view of a measuring-cell rotor (7) according to the invention, with a plurality of measuring cells (6) arranged in an arc-shaped fashion, wherein each measuring cell (6) comprises a first chamber (61) for accommodating a platelet-containing liquid sample and a second chamber (62), which catches the liquid sample from the first chamber provided that a centrifugal force acts on the measuring cell. The measuring cell furthermore comprises a porous partition member (63), which separates the first and second chambers from one another over the entire diameter of the hollow body. The partition member (63) contains at least one soluble substance that influences the platelet activity.

The measuring cells (6) have a curved shape along their longitudinal axis. The region of a measuring cell (6), which contains the partition member (63), has a smaller diameter than the remaining regions of the measuring cell. In the upper side of the measuring-cell rotor (7) there are pipetting holes (68), through which the sample material can be introduced into the first chamber (61) of a measuring cell (6). The arrow indicates the rotational direction of the measuring-cell rotor (7).

LIST OF REFERENCE SIGNS

Measuring cell 1, 2, 3, 4, 5, 6
Measuring-cell rotor 7
First chamber for accommodating a sample 11, 21, 31, 41, 51, 61
Second chamber for catching the sample from the first chamber 12, 22, 32, 42, 52, 62
Partition member 13, 23, 33, 43, 53, 63
Means for subdividing the space in the second chamber 24, 34, 44, 54
First portion of the second chamber (capture region) 221, 321, 421, 521
Second portion of the second chamber (measuring region) 222, 322, 422, 522
Electrode 25, 35, 45
Sample liquid 29, 39, 49, 59
First section of means for subdividing the space in the second chamber 341
Second section of means for subdividing the space in the second chamber 342
Wall 36
Third portion of the second chamber (overflow region) 523
Opening 57
Pipetting hole 68

The following exemplary embodiment serves to illustrate the method according to the invention and should not be construed as being restrictive.

EXAMPLES

Example 1

Determining the Platelet Activity in a Whole-Blood Sample, According to the Invention Measuring cells according to the invention were produced as follows: conically shaped centrifuge tubes (50 ml Falcon tubes made of transparent plastic, Becton Dickson) were cut off approximately halfway up. A single-use filter attachment with a PVDF membrane (Millipore Millex®-SV, 5 µm pore dimensions) was attached to the opening of a cut-off Falcon tube. According to the invention, the PVDF membrane was pretreated using a platelet activator mixture containing collagen and epinephrine (respectively 0.5 mg/ml). To this end, 0.8 ml of the mixture was placed over a Millipore Millex®-SV single-use filter attachment and subsequently air-dried. As a control, 0.8 ml of water was placed over a Millipore Millex®-SV single-use filter attachment and subsequently air-dried. A single-use syringe made of plastic (Omnifix®, 5 ml, B. Braun Melsungen AG), without piston and injection needle, was now attached to the Millipore Millex®-SV single-use filter attachment attached to the cut-off Falcon tube.

Now, 1.5 ml of a normal citrate blood sample were introduced into the first chamber of the measuring cell, the single-use syringe, and the measuring cell was centrifuged for 75 seconds with 50×g at 22° C. in a centrifuge (Rotixa R50, Andreas Hettich GmbH & Co. KG). The amount of liquid caught in the second chamber, the cut-off Falcon tube, was determined volumetrically.

It can be seen from table 1 that the use of partition members impregnated by the platelet activators collagen and epinephrine results in a reduced flow of sample liquid due to the platelet aggregation induced in the blood sample.

TABLE 1

| Impregnation of the partition member | Flow volume |
| --- | --- |
| Collagen/Epinephrine | 0.6 ml |
| Water | 1.5 ml |

The invention claimed is:

1. A measuring cell for determining platelet function, wherein the measuring cell is configured to be received in a centrifuge, and
wherein the measuring cell comprises:
a first chamber for accommodating a platelet-containing liquid sample,
a second chamber which catches the liquid sample from the first chamber upon a centrifugal force of 50-2000 times gravity acting on the measuring cell, and
a porous partition member comprising a structure that completely separates the first and second chambers from one another, wherein the porous partition member includes a plurality of pores having a pore dimension of 2-20 µm sufficient for passage of individual blood cells while preventing passage of cell aggregates, wherein the pore dimension of 2-20 µm allows forced passage of individual blood cells upon the centrifugal force of 50-2000 times gravity acting on the measuring cell and resists the passage of individual blood cells in the absence of the centrifugal force,
wherein the structure of the porous partition member defines no perforations, cuts, or apertures apart from the plurality of 2-20 µm pores, and
wherein the partition member contains at least one soluble substance that influences the platelet activity.

2. The measuring cell as claimed in claim 1, wherein the at least one soluble substance that influences the platelet activity is a platelet activator, from the following group: ADP, 2-MeSADP, collagen, epinephrine, ristocetin, thrombin, TRAP, arachidonic acid, U46619, PMA and serotonin.

3. The measuring cell as claimed in claim 1, wherein the at least one soluble substance that influences the platelet activity is a platelet inhibitor, from the following group: prostaglandin E1, prostaglandin 12, forskolin, iloprost and cicaprost.

4. The measuring cell as claimed in claim 1, wherein the partition member additionally contains calcium chloride ions.

5. The measuring cell as claimed in one claim 1, wherein at least one partial section of the second chamber consists of a light-transmitting material.

6. The measuring cell as claimed in claim 1, wherein a plurality of electrode pairs are arranged on the second chamber for electrically measuring the filling level.

7. The measuring cell as claimed in claim 1, wherein the second chamber which starting from the porous partition member, has a proximal half and a distal half along the longitudinal axis thereof, has means in the interior for subdividing the space in the second chamber into a first portion and a second portion, wherein the first portion serves to capture and transport the sample liquid that passes through the partition member, and wherein the second portion serves to measure the amount of liquid in the sample liquid caught in the second chamber, and wherein the first and second portions are interconnected in the distal half of the second chamber such that the caught and transported sample liquid can pass into the second portion from the first portion.

8. The measuring cell as claimed in claim 7, wherein the means for subdividing the space in the second chamber into a first and a second portion has a plane that is at an angle relative to the porous partition member and extends from the proximal into the distal half of the second chamber.

9. The measuring cell as claimed in claim 7, wherein the means for subdividing the space in the second chamber into a first and a second portion has a first section, which has a plane that is at an angle relative to the porous partition member, and has a second partial section which follows the first partial section, runs substantially parallel to a wall delimiting the space in the second chamber and forms a tubular structure with said wall, which tubular structure extends into the distal half of the second chamber.

10. The measuring cell as claimed in claim 7, wherein the means for subdividing the space in the second chamber into a first and a second portion has a funnel-like shape, and the tubular region of the funnel-like means extends into the distal half of the second chamber.

11. The measuring cell as claimed in claim 7, wherein the second portion of the second chamber, which serves to measure the amount of liquid in the sample liquid caught in the second chamber, has means for electrically measuring the filling level.

12. The measuring cell as claimed in claim 1, wherein the second chamber which starting from the porous partition member, has a proximal half and a distal half along the longitudinal axis thereof, has means in the interior for subdividing the space in the second chamber into a first, a second and a third portion, wherein the first portion serves to capture and transport the sample liquid that passes through the partition member and wherein the sample liquid is transported along the longitudinal axis of the second chamber into the distal from the proximal half, and wherein the second portion serves to measure the flow speed of the sample liquid captured in the second chamber, and wherein the third portion serves as an overflow for the sample liquid from the second portion, and wherein the first and second portions are interconnected in the distal half of the second chamber such that the sample liquid caught and transported can pass into the second portion from the first portion, and wherein the second portion has the form of a capillary, which rises from the distal half in the direction of the proximal half of the second chamber and has an opening at its end, which opening establishes a connection to the third portion.

* * * * *